Jan. 7, 1964 W. FLEMER III Plant Pat. 2,338
PAGODA TREE
Filed Jan. 17, 1963
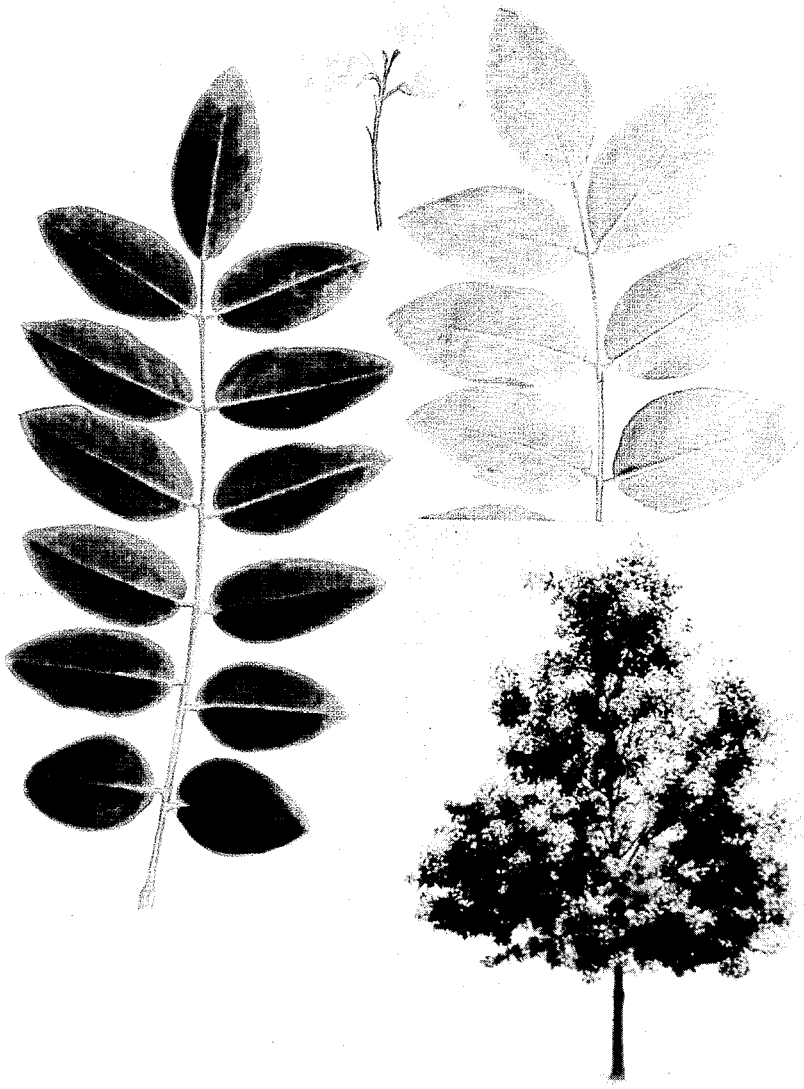
Inventor.
William Flemer III
By: Robb & Robb
Attorneys.

United States Patent Office

Plant Pat. 2,338
Patented Jan. 7, 1964

2,338
PAGODA TREE

William Flemer III, Princeton, N.J., assignor to Princeton Nurserymen's Research Associates, Princeton, N.J., a partnership Filed Jan. 17, 1963, Ser. No. 252,263
1 Claim. (Cl. Plt.—51)

The present invention relates to a new and distinct variety of pagoda tree, botanically known as *"Sophora japonica,"* which originated as a selected seedling derived from open-pollinated seedlings of the pagoda tree variety named "Trinity" (unpatented and also known as P.N. No. 36–4).

At the time this new variety was discovered by me, I was engaged in growing a block of open pollinated seedlings of the parent variety "Trinity," in the nursery of my assignee in the township of Plainsboro, State of New Jersey. My attention was attracted to a particular seedling tree by virtue of the fact that it appeared to be at least one-third (⅓) larger than the average of the other trees in the same block, and also by virtue of the fact that the tree bore exceptionally glossy, large foliage and was completely free of leaf hopper injury which affected the sibling seedlings in the same block. I thereupon took steps to preserve this particular seedling, keep it under observation, and, in due course, I asexually reproduced the same by budding, as performed in the nursery aforementioned, in the township of Plainsboro, State of New Jersey. Continued observations of the original seedling, and the progeny thereof, showed additional important characteristics which differentiated the new seedling variety from all other varieties. Although the male parent of the new open-pollinated seedling is unknown to me, I am convinced that the new seedling represents a new and distinct variety by virtue of the following unique combination of outstanding characteristics which distinguish it from all other varieties of which I am aware:

(1) A rapid habit of growth, with consequent attainment of substantially larger than average size of other pagoda tree varieties;

(2) Straight central trunk which is attained without the frequent pruning and costly staking that is usually necessary to grow shapely trees of ordinary pagoda tree seedlings;

(3) An upright ovate tree crown which is far better suited to street tree planting than the irregular spreading shapes of ordinary pagoda tree varieties;

(4) Glossy, large, lustrous and attractive Dark Green foliage; and (5) Good insect resistance and especially resistant to leaf hopper feeding activities, as determined by comparison with other seedlings grown under the same cultural conditions in adjacent nursery rows in the State of New Jersey.

The accompanying drawing shows a typical specimen tree, as depicted in black and white to illustrate its form and general habits of growth, as well as typical specimens of the foliage and flowers as depicted in color, with the foliage specimens illustrating both the upper and under surfaces of the leaflets.

The following is a detailed description of my new pagoda tree variety, with color terminology in accordance with the Munsell Color Chart, except where general color terms of ordinary dictionary significance are obvious:

Parentage: A selected open-pollinated seedling of "Trinity."

Propagation: Holds its distinguishing characteristics through succeeding propagations by budding (sometimes termed bud-grafting).

Locality where grown and observed: Township of Plainsboro, Plainsboro, New Jersey.

Tree: Large size; vigorous; with a central leader; compact oval head; rapid growing; hardy; moderately productive of fruits; regular bearer.

*Trunk.*—Medium thickness; smooth.

*Branches.*—Thick; smooth-barked; open-branching; excurrent pattern of branching in young specimens. Bark color (1-year wood)—Dark Olive Green, Plate 10.0GY3/4.

*Lenticels.*—Scattered; small.

Foliage:

*Leaves.*—Compound of 11–13 leaflets, length along midrib 18 to 20 cm.; width from tip of leaflet to tip of opposite leaflet from 8 to 10.5 cm.; length of individual leaflets along midrib from 4.5 to 6 cm.; width of individual leaflets from 2 to 2.5 cm.; large for species; ovate; subcordate at the base; thick; leathery. Upper surface—Lustrous. Under surface—glaucous; minutely pubescent. Margin—entire. Color—mature: upper surface—Dark Green, Plate 10.0GY3/2; under surface—Pale Bluish Green, Plate 10.0GY6/2. Midrib veins—color: Yellow Green, Plate 7.5GY6/10. Petiole—of entire leaf: short (from 2 to 2.5 cm.), moderately thick; of individual leaflets: from .25 to .3 cm. long.

Flowers: Mid season, as compared to other varieties; large; fragrant; borne in large, loose terminal panicles of from 1100 to 1500 flowers per panicle.

*Panicles.*—Length—from 30 to 40 cm. Width—from 38 to 42 cm.

*Individual flowers.*—Length—2 cm. Width—1.5 cm.

*Wings.*—Color—Pale Yellow, Plate 7.5Y8/4, with a yellow blotch at base corresponding to Plate 7.5Y8/10.

*Keel.*—Color—Medium Rosy Pink, Plate 2.5RP7/6.

Fruit: Not significant; curved; stipitate pod; constricted between individual seeds; from 3 to 5 seeds per pod.

Insect resistance: Especially good resistance to injury and stunting due to leaf hopper feeding activities, as determined by comparison with other varieties grown under the same conditions in the State of New Jersey.

I claim:

A new and distinct variety of pagoda tree, substantially as herein shown and described, characterized particularly as to novelty by the unique combination of a rapid habit of growth and relatively large size, a naturally straight central trunk; an upright and ovate tree crown, exceptionally glossy, large, lustrous and attractive Dark Green foliage, and especially good resistance to injury and stunting due to leaf hopper feeding activities.

No references cited.